(12) United States Patent
Kappel et al.

(10) Patent No.: US 10,653,436 B2
(45) Date of Patent: *May 19, 2020

(54) MEDICAL DEVICE FOR CUTTING

(71) Applicant: Boston Scientific Scimed, Inc., Maple Grove, MN (US)

(72) Inventors: Gary S. Kappel, Acton, MA (US); Sean P. Fleury, Brighton, MA (US); Paul Smith, Smithfield, RI (US); Brandon M. Zalewski, Clinton, MA (US); Laurie A. Soderbom, Nashua, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

This patent is subject to a terminal disclaimer.

(21) Appl. No.: 15/631,409

(22) Filed: Jun. 23, 2017

(65) Prior Publication Data

US 2017/0281148 A1 Oct. 5, 2017

Related U.S. Application Data

(63) Continuation of application No. 13/773,440, filed on Feb. 21, 2013, now Pat. No. 9,717,518.

(Continued)

(51) Int. Cl.
*A61B 18/14* (2006.01)
*A61B 17/295* (2006.01)
*A61B 17/3201* (2006.01)
*A61B 17/32* (2006.01)
*A61B 17/29* (2006.01)

(Continued)

(52) U.S. Cl.
CPC ...... *A61B 17/320016* (2013.01); *A61B 17/29* (2013.01); *A61B 17/295* (2013.01); *A61B 17/3201* (2013.01); *A61B 18/12* (2013.01); *A61B 18/1445* (2013.01); *A61B 17/0218* (2013.01); *A61B 2017/00296* (2013.01); *A61B 2017/00353* (2013.01); *A61B 2017/2936* (2013.01); *A61B 2017/320044* (2013.01);
(Continued)

(58) Field of Classification Search
CPC . A61B 18/1445; A61B 18/1442; A61B 18/12; A61B 17/29; A61B 17/295; A61B 17/3201; A61B 17/320016; A61B 2017/2945; A61B 2017/0353; A61B 2018/1445; A61B 2018/00601; A61B 2018/1312; A61B 2018/146
See application file for complete search history.

(56) References Cited

U.S. PATENT DOCUMENTS 4,326,335 A    4/1982  Morton
6,063,082 A *  5/2000  DeVore .............. A61B 17/3468
                                                            606/170
(Continued)

*Primary Examiner* — Nadia A Mahmood
*Assistant Examiner* — Pamela M. Bays
(74) *Attorney, Agent, or Firm* — Bookoff McAndrews, PLLC

(57) ABSTRACT

A medical device including an elongate member having a proximal end and a distal end and an end-effector disposed at the distal end of the elongate member is disclosed. The end-effector further includes a plurality of arms, which may pivot or move relative to one another. Further, each arm includes an inner edge defining a cutting edge, and an outer edge having at least one geometric feature for manipulating tissue.

5 Claims, 4 Drawing Sheets

Related U.S. Application Data

(60) Provisional application No. 61/601,868, filed on Feb. 22, 2012.

(51) Int. Cl.
| | | |
|---|---|---|
| *A61B 18/12* | (2006.01) | |
| *A61B 17/00* | (2006.01) | |
| *A61B 17/02* | (2006.01) | |
| *A61B 18/00* | (2006.01) | |

(52) U.S. Cl.
CPC ........... *A61B 2018/00595* (2013.01); *A61B 2018/146* (2013.01); *A61B 2018/1422* (2013.01)

(56) References Cited

U.S. PATENT DOCUMENTS

| | | | |
|---|---|---|---|
| 2001/0021861 A1* | 9/2001 | Boebel | A61B 17/29 606/207 |
| 2002/0188294 A1 | 12/2002 | Couture et al. | |
| 2004/0243125 A1* | 12/2004 | Dycus | A61B 18/1445 606/51 |
| 2005/0070764 A1 | 3/2005 | Nobis et al. | |
| 2007/0173814 A1 | 7/2007 | Hixson et al. | |
| 2007/0179525 A1* | 8/2007 | Frecker | A61B 17/29 606/205 |
| 2010/0057085 A1* | 3/2010 | Holcomb | A61B 18/1445 606/51 |
| 2010/0234743 A1 | 9/2010 | Stewart et al. | |
| 2010/0234843 A1* | 9/2010 | Stewart | A61B 17/00008 606/46 |
| 2010/0256523 A1 | 10/2010 | Uznanski et al. | |

* cited by examiner

MEDICAL DEVICE FOR CUTTING

CROSS-REFERENCE TO RELATED APPLICATIONS

This application is a continuation of U.S. application Ser. No. 13/773,440, filed on Feb. 21, 2013, now issued as U.S. Pat. No. 9,717,518, which claims the benefit of priority of U.S. Provisional Application No. 61/601,868, filed on Feb. 22, 2012, which are incorporated by reference herein in their entireties.

FIELD OF THE INVENTION

Embodiments of the present disclosure relate generally to medical devices suitable for use in surgical procedures. In particular, embodiments of the instant disclosure relate to minimally-invasive multi-functional medical devices employed for body tissue manipulation.

BACKGROUND OF THE INVENTION

Minimally invasive procedures involve indirect observation of a surgical field through an endoscope or similar device inserted through an incision or a natural anatomical opening. Endoscopes provide platforms for employing numerous tools, such as minimally-invasive surgical instruments, e.g., to sever, remove, examine, and/or otherwise manipulate objects from inside the body. The item to be retrieved can be a natural object, such as a blood clot, tissue, stone, or polyp; or a foreign object, such as a coil, stent, or guidewire.

Most of the instruments employed for minimally invasive procedures, perform a single function by design, and may need to be exchanged with a second device if another function is to be performed during the endoscopic procedure.

Single function instruments increase the cost of the surgery because they increase the procedure time due to exchanges, handling time and increase the number of instruments needed to complete the surgery. Exchanging instruments during a procedure may further cause inaccuracies in the placement and location of the distal tip within the body lumens, disrupt a surgeon's concentration, and add to the procedure time. These factors risk patient's safety. In addition, where disposable instruments are used, using multiple devices for the same procedure may increase waste.

Thus, there exists a need for multi-functional end-effectors having critical multi-functional capability at a critical time during procedures, allowing safer, quicker, and efficient medical procedures.

SUMMARY OF THE INVENTION

Embodiments of the disclosure provide a medical device with a multifunctional end-effector.

In accordance with an aspect of the present disclosure a medical device may include an elongate member having a proximal end and a distal end and an end-effector disposed at the distal end of the elongate member. The end-effector may include a plurality of arms (e.g., jaws or blades) configured to pivot or move relative to one another. Each arm may include an inner edge defining a cutting edge, and an outer edge having at least one geometric feature or configuration for manipulating tissue.

In various embodiments, the medical device may include one of the following additional features: the arms may be blades; the plurality of arms may include two arms, wherein the two arms are both configured to pivot relative to one another, the outer edge of one of the arms may include a hook; the hook may be an electrocautery hook; the geometric feature may comprise serrations for grasping tissue; the arms may be curved in a direction at an angle to the pivoting axis; the inner edge may include serrated teeth; and the outer edge may include a blunt surface configured to facilitate dissection of tissue along natural tissue layers.

In accordance with another aspect of the disclosure, an apparatus for manipulating tissue may include an elongate member having a proximal end and a distal end and a pair of scissors disposed at the distal end of the elongate member. The scissors may include two blades, wherein at least one of the blades is configured to rotate relative to the other blade, each blade having an inner edge and outer edge, with the inner edges cooperating for cutting tissue, and each outer edge including a geometric feature configured to manipulate tissue.

In various embodiments, the apparatus may include one or more additional features: the inner edge may include serrated teeth; the outer edge may include a hook; the scissors may include a coating; the outer edge may include barbs for grasping tissue; and the scissors may include radiopaque markers.

In accordance with an alternate aspect of the disclosure, a method of manipulating tissue may include introducing a medical device into the body. The medical device may include an elongate member having a proximal end and a distal end, and a scissors disposed at the distal end of the elongate member. The scissors may include two blades, wherein at least one of the blades is configured to rotate relative to the other blade. Each blade may include an inner edge and outer edge, the inner edges cooperating for cutting tissue, and each outer edge including a geometric feature configured to manipulate tissue. The method may further include advancing the medical device to a desired location within the body, opening the blades, and manipulating tissue.

In various embodiments, the method may further include one or more of the following aspects: severing tissue with the inner edges of the arms; manipulating the severed tissue with the outer edges of the arms; and the outer edge may include barbs for grasping tissue.

Additional objects and advantages of the disclosure will be set forth in part in the description, which follows, and in part will be evident from the description, or may be learned by practice of the disclosed subject matter. The objects and advantages of the disclosed subject matter will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments of the disclosure and together with the description, serve to explain the principles of the claimed invention.

DESCRIPTION OF THE EMBODIMENTS

Reference will now be made in detail to embodiments of the disclosure, an example of which is illustrated in the accompanying drawings. Wherever possible, the same reference numbers will be used throughout the drawings to refer to the same or like parts.

Overview

Embodiments of the present disclosure relate to medical devices with multi-functional end-effectors for endoscopic instruments, where it may be desirable to perform medical procedures having several different functionalities. To accomplish that goal, in one embodiment of the disclosure, the medical device generally includes two blades, pivotally mounted at the distal end of the endoscopic instrument. Inner edges of the two blades may be sharpened cutting edges, together defining scissors (e.g., a pair of scissors) for severing tissue. The outer edges of each blade can take a number of forms, each designed to perform a specific tissue manipulation function. For example, outer edges may contain serrations capable of grabbing and/or retaining tissue. A wide variety of particular forms of the blade outer surface would be understood by a person skilled in the art. As used in this disclosure, "distal" refers to a position or direction further from the user, and "proximal" refers to a position or direction opposite "distal" and closer to the user.

Exemplary Embodiments

Figure 1A:
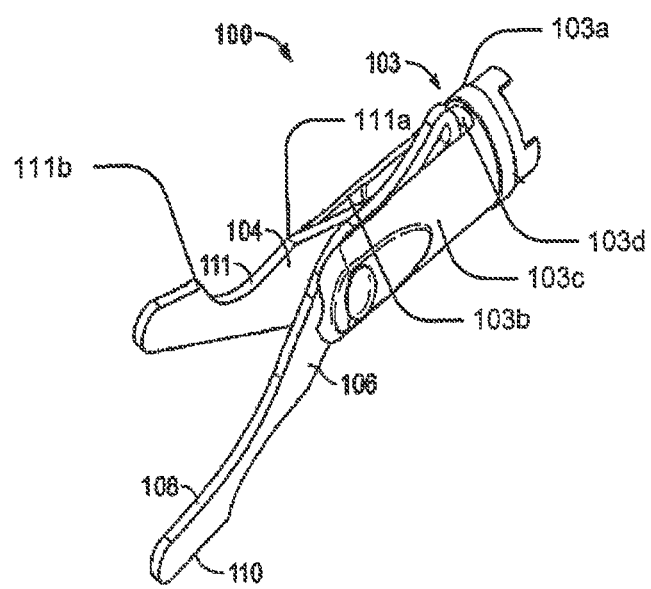
FIGS. 1A and 1B illustrate an exemplary multi-functional end-effector, according to an embodiment of the disclosure.
Figure 1B:
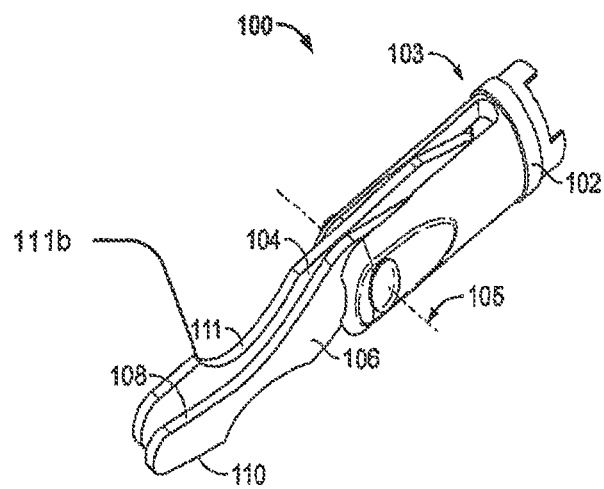

FIGS. 1A and 1B illustrate an exemplary multi-functional end-effector 100, depicted in open and closed configurations, respectively. End-effector 100 may be disposed at a distal portion of an elongate member (not shown). End-effector 100 may include a clevis 103 extending from a distal end of the elongate member. The clevis 103 may include a substantially circular portion 103a configured for connection to the elongate member, and a plurality of extensions 103b, 103c extending distal from circular portion 103a. As would be understood by those of skill in the art, portion 103a may have any other desired geometry and shape. Extensions 103b, 103c may define a longitudinal slot 103d. The end-effector 100 may further include two arms 104, 106 disposed within slot 103d and rotatably connected to one or both of extensions 103b, 103c. Arms 104, 106 may be connected to clevis 103 by any suitable means, including, but not limited to, a pivot pin. In some embodiments, both arms 104, 106 may be configured to move relative to one another. In other embodiments, one of arms 104, 106 may be fixed while the other of arms 104, 106 may be configured to move relative to the fixed arm. It should be noted that in some embodiments, the "arms" can also be referred to as "blades." For consistency, the former term will be employed herein.

In the illustrated embodiment, arms 104, 106 are elongated, generally rigid members with a flattened cross-sectional shape. The elongate structure of the arms 104, 106 includes an inner edge 108 and an outer edge 110. Design elements to be considered in selecting particular arms 104, 106 include the length of the elements, dictated primarily by the desired manipulation; the shape of the elongated portion, which can be generally planar, tubular, or rounded, as known in the art; the inner edge 108, which may define a cutting edge; and the outer edge 110, which may include one or more geometric features to allow grasping, retaining, positioning, and/or severing tissue. The cutting edge may extend along the entire length of the inner edge 108 or only a portion of inner edge 108 may be configured as the cutting edge.

The end-effector 100 and its related components may be formed of any suitable biocompatible material known in the art. For example, the material may be nitinol or stainless steel. Furthermore, the end-effectors may comprise polymers, ceramics, other metals, or any other combinations thereof. The material can be selected from among those generally available to the art based on desired stiffness, resilience, and other properties of the arms. Those factors, as well as compatibility with remaining portions of the medical device, may well be within the skill of those in the art. The end-effector 100 and its related components may be fabricated using a Micro-Fabric MEMS type process.

In the open position depicted here, the end-effector 100 is particularly adapted for severing tissue, in the manner of a scissors. To that end, the cutting edge on each blade may be formed by beveling that edge, leaving the side of the arms facing one another relatively flat. Thus configured, the operator can sever tissue by opening and closing the blades, as shown successively in FIGS. 1A and 1B. Alternatively, the inner edge may be configured for blunt dissection.

FIG. 1B illustrates the end-effector 100 in a closed configuration, with arms 104, 106 overlapping one another. Indeed, if desired, end-effector 100 can be completely retracted, and in one embodiment of the present disclosure end-effector 100 can be completely withdrawn into an endoscope, a suitable introduction sheath, or similar instrument (not shown). The retracted configuration could prove useful for moving the unit through a patient's body lumens in preparation for use.

In either the open or closed position, end-effector 100 can accomplish a number of tissue manipulation tasks in addition to severing tissue. The ability to perform particular manipulation tasks is enhanced by providing arms 104, 106 with particular configurations of the outer edges 110 of each blade. In the example shown, the outer edges 110 include scalloped areas 111 for grasping or retaining tissues, for separating vessels, or otherwise manipulating bodily structures. Alternatively, the outer edges 110 may include roughened surface or a coating to increase the tissue adherence ability of the end-effector 100. In some embodiments, the medical device may be capable of conducting electromagnetic energy, such as, radio frequency or laser energy. In another embodiment, cauterization features may be incorporated by addition of an hook 111b, such as an electrocautery hook, to the outer edges of scalloped area 111. In this embodiment, the inner edges of arms 104, 106 could be formed of insulated or non-conductive material, for example, ceramic or any other suitable material known in the art for protecting tissue. Alternatively, the scissor blades may be configured to conduct energy.

In addition, the arms 104, 106 may have additional features, such as, hooks or other projections on the sidewalls for adhering or grasping tissue. In some embodiments, the features may include one or more of tabs, barbs, grooves, and holes. Alternatively, the arms 104, 106 may have a distally facing spear for skewering tissue. In another embodiment, the arms 104, 106 may have one or more scallops on the sidewalls to facilitate cutting.

Alternatively, the inner edge 108 and the outer edge 110 of each arm 104, 106 may include attachment means to allow additional functionalities to be selectively incorporated in the end-effector 100. For example, the inner and outer edges may have attachment means to attach blades for severing tissue and/or serrated teeth for grasping tissue, respectively. Those in the art can choose from among a number of attachment means, such as magnetic connection, a snap-fit connection, or an adhesive connection.

A control member (not shown), such as, a control cable, for example, may extend proximally through clevis 103 and the associated elongated member to allow an operator to move to selectively open and close arms 104, 106. Configuration and formation of such elements are known in the art and will not be further described further here.

Figure 2:
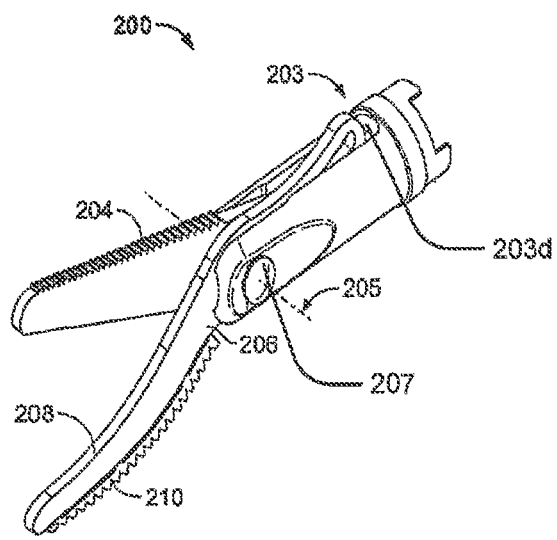
FIG. 2 depicts an alternative embodiment of an end-effector.

FIG. 2 depicts an alternative embodiment of an end-effector, in accordance with the present disclosure. Similar to the embodiment described in FIG. 1, the end-effector 200 may be formed by two arms 204, 206 extending distally from a slot 203d in clevis 203. The arms 204, 206 are pivotally mounted on a pivot pin 207. Each of the arms 204, 206 has an inner edge 208 and an outer edge 210. As depicted, inner edges 208 include blades for severing tissue, but outer edges 210 may be considerably wider than are the inner edges, and may include serrations adapted to grasp or retain tissue. As described earlier, the serrations may be formed directly in the blade, or they may be attached by snap-fit or other known attachment means known in the art. In some embodiments, the row of serrations may include any useful pattern including spaces, a blunt surface, or a taller or shorter serration in place of every other serration.

Figure 3:
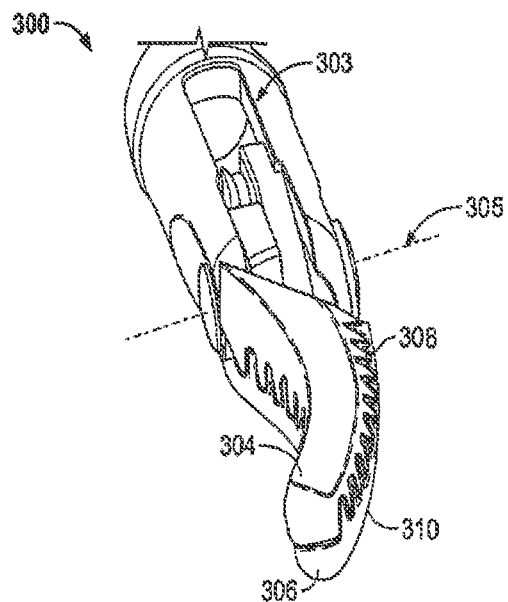
FIG. 3 illustrates yet another embodiment of an end-effector.

FIG. 3 illustrates a further alternative embodiment of an end-effector 300, in accordance to a further embodiment of the present disclosure. Similarly to the end-effectors described above in connection with FIGS. 1A-2, end-effector 300 may be formed of two arms 304, 306. The arms 304, 306 are pivotally connected generally near their proximal end and may be curved to form a 'C'-shaped structure, with its arc lying in a plane at an angle to the direction in which the arms 304, 306 pivot. Similarly, to the end-effector described in connection with FIG. 1, each of the arms 304, 306 has an inner edge 308 and an outer edge 310, which together form a cutter blade with serrated teeth. As shown, the serrated teeth mesh when the arms 304, 306 are closed. In some embodiments, the serrated teeth may include teeth in varying patterns including but not limited to spaces, a blunt end, a taller or shorter teeth. As would be understood by a person of ordinary skill in the art, the outer edges 310 may have many other functions including any one of the functionalities described in relation with FIG. 1.

When arms 304, 306 are in an open position, the teeth present on the inner edge 308 may be employed for a number of functions. For example, the teeth could be used to scrape tissue, a function which can be particularly useful in the vicinity of, e.g., the bile duct. In the closed configuration, the cutting teeth on the inner edges may overlap, forming a smooth outer surface. Other variations, featuring different sized serration teeth or varying patterns of teeth, for example, will be apparent to those of skill in the art.

Figure 4:
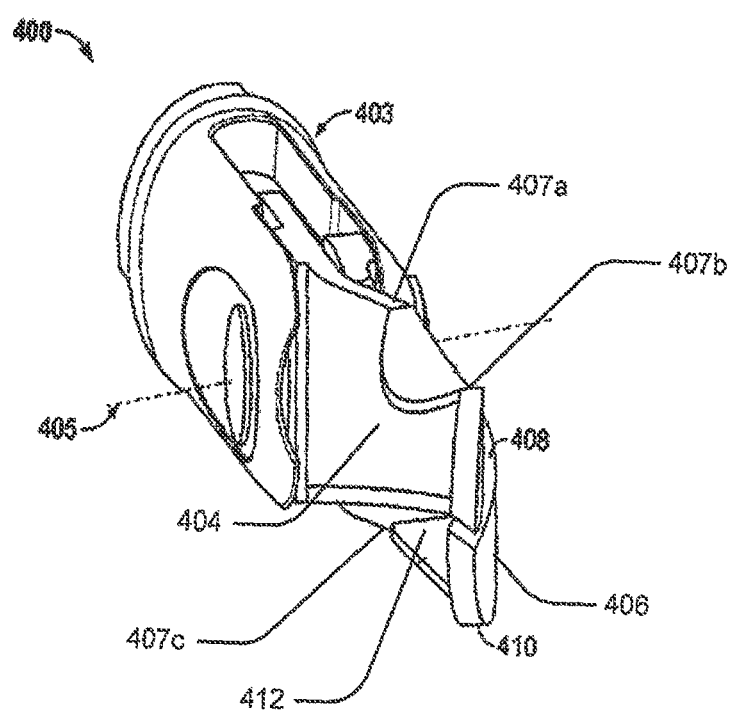
FIG. 4 depicts a further embodiment of an end-effector.

FIG. 4 depicts an embodiment of the end-effector of FIG. 1 with a flanged surface 412. Similar to the embodiment described in FIG. 1, the end-effector 400 may be formed of two arms 406, 406. As illustrated, the arms 404, 406 may have a curved shape with a relatively flattened cross-section. As described in FIG. 1, each of the arms 404, 406 may have an inner edge 408 and an outer edge 410. The Inner edges 408 and outer edges 410 form a curved structure with a wide flanged, scalloped backside for tissue separation. As would be evident to a person with ordinary skill in the art the Inner 408 and outer edges 410 may have any of the number of variations described in relation to FIG. 1.

Figure 5A:
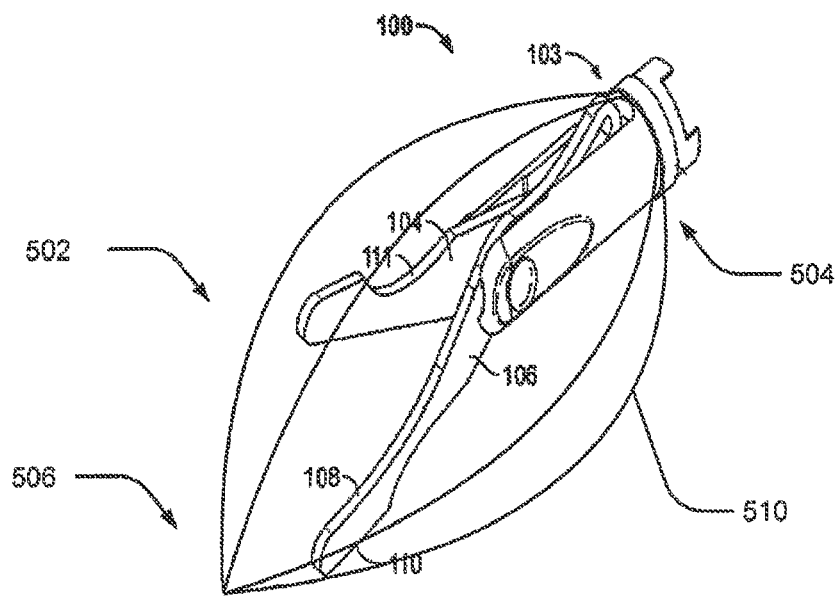
FIGS. 5A and 5B depict a further embodiment of an end-effector with a retractor feature, in accordance with an aspect of the present disclosure.
Figure 5B:
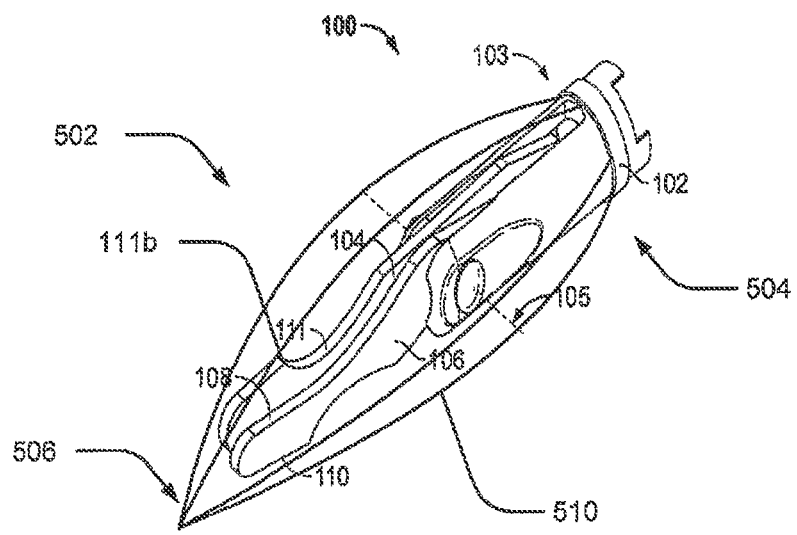

FIGS. 5A-5B are perspective views of an exemplary end-effector of FIG. 1 with a retractor feature. More particularly, FIG. 5A illustrates the end-effector 500 with retracting member 502 in the expanded state, and FIG. 5B illustrates the end-effector 500 with retracting member 502 in a compressed state. Here, end-effector 500 includes arms 104, 106 and retracting member 502, which has a proximal end 504 and a distal end 506 connected to circular portion 103a of the clevis 103. Retracting member 502 is configured as but not restructured to a basket 508 having multiple legs 510. The legs 510 are joined together along the longitudinal axis at the proximal and distal ends of the retracting member 502. In another embodiment, legs 510 may not be joined at the distal end, but flare out to push surrounding tissue outward and to provide space for the end-effector 100 to manipulate the desired tissue. In some embodiments, retracting member may comprises only two legs and functions as a snare to retrieve tissue or objects. It will be understood that other basket configurations are also within the scope of the present disclosure. In all basket embodiments, however, legs 510 remain substantially parallel to the longitudinal axis in the compressed state, and radially expand in the expanded state. Alternatively, the retracting member 502 may be rotatable axially around the end-effector 100 to allow tissue retraction from the desired side.

As depicted in FIG. 5B, the retracting member 502 may form a protective shield over the end-effector 100 while traversing through a working channel or a body lumen, protecting the channels and lumens from accidental ruptures. Each leg 510 may be formed of a single wire extending from the proximal end to the distal end. Wire may have any of a number of cross-sections such as round, rectangular, triangular, or arcuate. Alternatively, the legs 510 may be formed of multiple wires twisted or braided along the length of the retracting member. Other structural variations would be understood by a person skilled in the art. The wires could also have a flexible mesh attached to capture and hold small tissue. In some embodiments, the wire may include barbs or other projections to aid tissue gripping. Alternatively, wires may be electrocautery or sharp and rotatable for cutting tissue. In another embodiment, surface of wires may have features such as surface roughening or coatings to improve tissue grasping or tissue adherence.

The retracting member 502 may be expanded radially by actuating a control member (not shown). By radial expansion, the retracting member 502 can push outward surrounding tissue, and may provide space for the arms 104, 106 to sever the required tissue. The degree of expansion and the strength of the legs may determine the cavity area created by the retracting member 502. Alternatively, the legs 510 may be actuated to open at the distal end flaring in a concave or convex fashion. In some embodiments, the legs 510 may be spring-loaded such that the operator may actuate a spring (not shown) to radially expand or contract the legs 510. As would be understood by a person of skill in the art, the basket 502 may be formed of any suitable number of legs 510. In some embodiments, the legs may extend relatively parallel to each other or may cross each other by twisting around the perimeter of the basket 508.

The basket 508 may be used to hold and position tissue prior to and during manipulation or resection as well for assisting in tissue retraction. Once the arms 104, 106 have dissected the required tissue, the retracting member 502 may be compressed, such that it holds the dissected tissue within the legs 510. Subsequently, the retracting member 502 may be withdrawn or the entire endoscopic device 100 may be retracted proximally to remove the dissected tissue.

One implementation of the present disclosure provides an end-effector 100 coated with an antibacterial covering to inhibit bacterial growth on Its surface. The antibiotic coating may contain an inorganic antibiotic agent, disposed in a polymeric matrix that adheres the antibiotic agent to the end-effector surface. Further, a drug-releasing coating may also be applied to the outer surface of the end-effector, assisting in delivery of drugs to the severing site. In another alternative, imaging markers may be applied to the end-effector surface, to assist in locating the end-effector within the body. Radiopaque, sonoreflective, and/or any other suitable markers may be employed.

The end-effectors described in FIGS. 1-4 may be employed to perform surgical procedure in a body lumen through an exemplary medical device. The medical device may include a conventional endoscope or a sheath, a guide tube, an introducer, or a lumen in an instrument having end-effector at its distal end for retrieving and capturing tissue or other target objects from body lumens. End-effector 100 extends through lumen formed in sheath, and a connecting member operatively connects the end-effector to a control member 103, a proximal end of which may be operatively coupled to an actuation handle, an automated hand, or other conventional device for receiving and transmitting user input in an endoscope.

The medical device of the present disclosure may be used to carry out a variety of medical or non-medical procedures, including surgical and diagnostic procedures in a wide variety of bodily locations. For example, resection or cauterization of a variety of body organs, such as esophagus, stomach, bladder, or the urethra could be accomplished using the method discussed above. In addition, at least certain aspects of the aforementioned embodiments may be combined with other aspects of the embodiments, or removed without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical device comprising:
    a member having a proximal end and a distal end;
    an end-effector disposed at the distal end of the member, the end-effector including a first arm and a second arm, wherein the first arm is configured to pivot relative to the second arm, wherein radially inward facing edges of the first arm and the second arm are non-conductive such that upon application of an electrical current to the end-effector, the electrical current does not flow through the radially inward facing edges of the first arm and the second arm; and
    an expandable element having a proximal end and a distal end, wherein the proximal end of the expandable element is coupled to a proximal end of the end-effector, the expandable element is movable between a radially-collapsed configuration and a radially-expanded configuration, the expandable element has a plurality of legs circumferentially spaced from one another, and distal ends of the plurality of legs converge toward one another.

2. The medical device of claim 1, wherein the radially inward facing edge of at least one of the first arm or the second arm includes serrated teeth.

3. The medical device of claim 1, wherein each of the first arm and the second arm is coupled to a clevis.

4. The medical device of claim 1, wherein the radially inward facing edge of each of the first arm and the second arm includes a cutting edge.

5. The medical device of claim 1, further including a pivot pin, wherein the first arm and the second arm are coupled to one another via the pivot pin, the expandable element is coupled to the end-effector proximally of the pivot pin, and the distal end of the expandable element is distal to distal ends of the first arm and the second arm.

* * * * *